(12) United States Patent
Tucker

(10) Patent No.: US 8,022,265 B2
(45) Date of Patent: Sep. 20, 2011

(54) REDUCED WEIGHT DECONTAMINATION FORMULATION UTILIZING A SOLID PERACID COMPOUND FOR NEUTRALIZATION OF CHEMICAL AND BIOLOGICAL WARFARE AGENTS

(75) Inventor: Mark D. Tucker, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 344 days.

(21) Appl. No.: 12/269,070

(22) Filed: Nov. 12, 2008

(65) Prior Publication Data

US 2009/0291151 A1 Nov. 26, 2009

Related U.S. Application Data

(63) Continuation-in-part of application No. 12/124,191, filed on May 21, 2008, which is a continuation-in-part of application No. 10/251,569, filed on Sep. 20, 2002, now Pat. No. 7,390,432.

(51) Int. Cl.
*C01B 15/00* (2006.01)
*C01B 15/12* (2006.01)
*A62D 3/00* (2007.01)
*A62D 3/30* (2007.01)
*A62D 3/38* (2007.01)
*A61L 2/18* (2006.01)
*C11D 3/39* (2006.01)
*C11D 1/62* (2006.01)

(52) U.S. Cl. ............... 588/320; 252/186.26; 252/186.42; 588/400; 588/401; 588/406; 588/408; 588/409; 588/901; 510/110; 510/370; 510/372; 510/504

(58) Field of Classification Search ............... 588/320, 588/400, 401, 406, 408, 409, 901; 252/186.26; 252/186.42; 510/110, 370, 372, 504; 206/568
See application file for complete search history.

(56) References Cited

U.S. PATENT DOCUMENTS

| 5,462,692 A | * | 10/1995 | Roesler et al. | 424/64 |
| 6,566,574 B1 | | 5/2003 | Tadros et al. | |
| 6,723,890 B2 | | 4/2004 | Tucker et al. | |
| 7,064,241 B2 | * | 6/2006 | Brown et al. | 588/320 |
| 7,125,497 B1 | | 10/2006 | Tucker et al. | |
| 7,271,137 B2 | | 9/2007 | Tucker et al. | |
| 7,276,468 B1 | | 10/2007 | Tucker | |
| 7,282,470 B2 | | 10/2007 | Tucker et al. | |
| 7,390,432 B2 | | 6/2008 | Tucker | |
| 7,718,594 B1 | * | 5/2010 | Lawson et al. | 510/421 |

(Continued)

OTHER PUBLICATIONS

Lewis, Richard J., Sr. (2002) Hawley's Condensed Chemical Dictionary (14th Edition), John Wiley & Sons, Online @ http://knovel.com/web/portal/browse/display?_EXT_KNOVEL_DISPLAY_bookid=704&VerticalID=0, headword = formulation, (Knovel Release Date: Sep. 4, 2003; downloaded Dec. 19, 2010), pp. 1.*

*Primary Examiner* — Daniel S Metzmaier
(74) *Attorney, Agent, or Firm* — Olivia J. Tsai

(57) ABSTRACT

A reduced weight decontamination formulation that utilizes a solid peracid compound (sodium borate peracetate) and a cationic surfactant (dodecyltrimethylammonium chloride) that can be packaged with all water removed. This reduces the packaged weight of the decontamination formulation by ~80% (as compared to the "all-liquid" DF-200 formulation) and significantly lowers the logistics burden on the warfighter. Water (freshwater or saltwater) is added to the new decontamination formulation at the time of use from a local source.

10 Claims, 2 Drawing Sheets

U.S. PATENT DOCUMENTS

| | | | |
|---|---|---|---|
| 7,750,199 B1 * | 7/2010 | Tucker | 588/320 |
| 7,829,520 B1 * | 11/2010 | Lawson et al. | 510/421 |
| 2004/0022867 A1 * | 2/2004 | Tucker et al. | 424/616 |
| 2005/0074359 A1 * | 4/2005 | Krieger et al. | 422/28 |
| 2005/0109981 A1 * | 5/2005 | Tucker et al. | 252/186.38 |
| 2005/0163896 A1 * | 7/2005 | Man et al. | 426/332 |

* cited by examiner

REDUCED WEIGHT DECONTAMINATION FORMULATION UTILIZING A SOLID PERACID COMPOUND FOR NEUTRALIZATION OF CHEMICAL AND BIOLOGICAL WARFARE AGENTS

CROSS-REFERENCE TO RELATED APPLICATIONS

This application is a Continuation-in-Part of U.S. patent application Ser. No. 12/124,191, entitled "Reduced Weight Decontamination Formulation for Neutralization of Chemical and Biological Warfare Agents", filed on May 21, 2008, which application is a Continuation-in-Part of U.S. patent application Ser. No. 10/251,569, filed on Sep. 20, 2002, now U.S. Pat. No. 7,390,432, and the specifications thereof are incorporated herein by reference.

FEDERALLY SPONSORED RESEARCH

The United States Government has rights in this invention pursuant to Department of Energy Contract No. DE-AC04-94AL85000 with Sandia Corporation.

BACKGROUND OF THE INVENTION

Sandia National Laboratories has previously developed DF-200, an enhanced aqueous decontamination formulation for the neutralization of chemical and biological warfare agents and biological pathogens.

Two formulations associated with DF-200 are summarized below:

DF-200HF (Enhanced Formulation for High Foam Applications):
2.0% Variquat 80MC (cationic surfactant)
1.0% Adogen 477 (cationic hydrotrope)
0.4% 1-Dodecanol (fatty alcohol)
2.0% Polyethylene Glycol 8000 (polymer)
0.8% Diethylene Glycol Monobutyl Ether (solvent)
0.5% Isobutanol (solvent)
5.0% Bicarbonate salt (buffer and peroxide activator)
3.5% Hydrogen Peroxide (oxidant)
2.0% Propylene Glycol Diacetate or Glycerol Diacetate (peroxide activator)
10.0% Propylene Glycol (organic stabilizer)
~2.0% Potassium Hydroxide (pH adjustment)
Water (Remainder—~70%)
Note: The formulation can be adjusted to a pH value between 9.6 and 9.9; and is effective for decontamination of all agents tested.

DF-200NF (Enhanced Formulation for No Foam Applications):
2.0% Benzalkonium Chloride
2.0% Propylene Glycol Diacetate or Glycerol Diacetate
3.5% Hydrogen Peroxide
5.0% Potassium Bicarbonate
10.0% Propylene Glycol (organic stabilizer)
~2.0% Potassium Hydroxide
Water (Remainder—~75%)

A new form of the Sandia National Laboratories decontamination formulation (DF-200) is needed to meet the CBW agent decontamination requirements of the US Department of Defense (DoD), and other potential users, for significantly reduced weight and volume burdens. Of primary interest and benefit to the warfighter is the use of one formulation for battlefield and fixed site decontamination that is easily deployable, fast reacting, environmentally friendly with low toxicity and corrosivity properties, and that has a low logistics burden. Currently, the aqueous-based DF-200 is provided in an 'all-liquid' configuration where all water is included within the packaged formulation. The current decontamination formulation of the US DoD (EasyDECON™-200 and MDF-200 which are based on Sandia National Laboratories DF-200 Decontamination Formulation) contains approximately 75% water and is packaged, shipped, and stored with all the water as part of the formulation. Although this configuration of DF-200 makes it simple to use (by quickly mixing each of the three liquid parts) it requires a significant logistics burden since each gallon of the formulation weighs approximately 9 lbs.

A new configuration of the decontamination formulation is needed that can be packaged as a dry kit, with most or all water removed, thereby reducing the packaged weight of the decontamination formulation by ~80% (as compared to the "all-liquid" DF-200 formulation) and significantly lowering the logistics burden on the warfighter. Water (freshwater or saltwater) would be added to the new decontamination formulation configuration at the time of use from a local source.

Currently, standard DF-200 is used by the military in an 'all-liquid' configuration consisting of three parts:
Part A: Foam Component (~49% by volume)—consists of surfactants, solvents, inorganic bases, and buffers dissolved in water;
Part B: 8% Hydrogen Peroxide Solution (~49% by volume)—consists of hydrogen peroxide dissolved in water; and
Part C: Liquid Peroxide Activator (~2% by volume)—consists of an organic liquid.

As seen in the current formulations above, water makes up a substantial portion of DF-200 and, hence, it removal can achieve the desired weight savings. However, development of a reduced weight configuration of DF-200 (i.e., a 'dry' formulation) is a considerable technical challenge. Ideally, a 'dry' formulation would have the following desirable characteristics:
high storage stability in extreme temperature environments;
rapid solubility of the ingredients in both freshwater and saltwater;
low cost (e.g., use of commercially available ingredients);
high efficacy against both chemical and biological warfare agents;
ability to maintain sufficient contact time between the formulation and the agents on both vertical and horizontal surfaces in all deployment conditions;
ability to be easily deployed with existing military equipment.

To accomplish these objectives, the development of a reduced weight decontamination formulation utilizing a solid peracid compound focused on three tasks:
evaluation of the sodium borate peracetate material to determine its stability under high temperature storage conditions;
selection of ingredients to extract chemical and biological warfare agents from contaminated material surfaces into the decontamination formulation for subsequent neutralization (i.e., selection of surfactants for incorporation into the decontamination formulation); and
selection of ingredients to enable the decontamination formulation to maintain sufficient contact time on a surface to achieve the required efficacy against chemical and biological warfare agents.

SUMMARY OF THE INVENTION

The present invention relates to a reduced weight decontamination formulation that utilizes a solid peracid compound (sodium borate peracetate) that can be packaged with all water removed. This reduces the packaged weight of the decontamination formulation by ~80% (as compared to the "all-liquid" DF-200 formulation) and significantly lowers the logistics burden on the warfighter. Water (freshwater or saltwater) is added to the new decontamination formulation at the time of use from a local source.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

The use of powdered additives to 'dry-out' some components certain ingredients of standard DF-200 formulations has been described in detail in commonly-owned U.S. Pat. Nos. 7,276,468 and 7,282,470 to Tucker, which are both incorporated herein by reference.

Neutralization is defined as the mitigation, de-toxification, decontamination, or otherwise destruction of TICs to the extent that the TICs no longer cause adverse health effects to humans or animals. The present invention addresses the need for decontamination formulations that are non-toxic, non-corrosive, lost-cost, long shelf-life, and that can be delivered by a variety of means and in different phases, including sprays, foams, fogs, mists, aerosols, gels, creams, pastes, baths, strippable coatings, etc.

The word "formulation" is defined herein as the made-up, "activated" product or solution (e.g., aqueous decontamination solution) that can be applied to a surface or body, or dispersed into the air, etc. for the purpose of neutralization, with or without the addition of a gas (e.g., air) to create foam. Unless otherwise specifically stated, the concentrations, constituents, or components listed herein are relative to the weight percentage of the made-up, activated aqueous decontamination solution. The word "water" is defined herein to broadly include: pure water, tap water, well water, waste water, deionized water, demineralized water, saltwater, or any other liquid consisting substantially of $H_2O$.

Evaluation of the High Temperature Stability of Sodium Borate Peracetate

Figure 1:
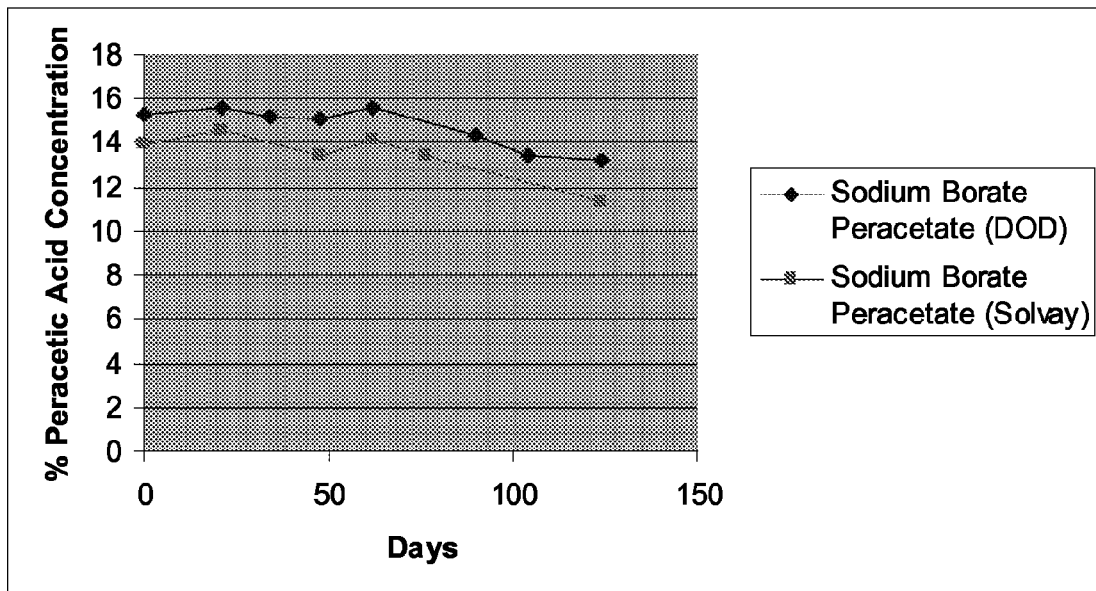
FIG. 1: Results from oven stability testing on sodium borate peracetate.

A primary consideration for the reduced weight decontamination formulation was to identify a solid oxidant material that is stable under high temperature storage conditions. In this case, the focus was on the peracid compound: sodium borate peracetate, $Na_2B_4O_5(OH)_4 \cdot 2CH_3COOH \cdot 2CH_3COO_2H$, also known as peracetyl borate (PAB), PES-SOLID, PBS-AC, and Sodium borate: peroxyacetic acid adduct; and has a molecular weight of 509.5. Two different sodium borate peracetate samples were obtained—one from the US DoD and one from Solvay, Inc (the manufacturer of the compound). Oven testing was initiated to test this material. The compound was placed in an oven that cycled between 30° C. and 70° C. on a 24-hour basis. The compound was placed in glass vials with plastic lids. The plastic lids were loosened slightly to provide a mechanism for pressure relief in the vials. Small samples of sodium borate peracetate were extracted from the oven approximately every seven days and the samples were analyzed for peracetic acid content via a titration method to determine if any degradation occurred. The results from the oven tests are shown in FIG. 1. The results show that sodium borate peracetate is relatively stable under these conditions. It retained approximately 80% of its original peracetic acid content even after 120 days of exposure to the high temperature storage conditions.

Description of Reaction Mechanisms in the Decontamination Formulation

The primary mechanism for detoxification of chemical agents in this decontamination formulation involves the principle of micellar catalysis. This principle is illustrated for a chemical agent that has low solubility in water that may be detoxified by nucleophilic or oxidative attack. A set of constituents has been selected in the decontamination formulation to provide a mechanism to solubilize the sparingly soluble chemical agent and to attract a reactive catalyst, dissolved in aqueous media, to a position in close proximity to the chemical molecule vulnerable to nucleophilic or oxidative attack. This is accomplished through the recognition that certain nucleophiles and oxidants are negatively charged. Therefore, the formulation contains cationic surfactants that form positively-charged micelles to solubilize the chemical agent and attract the negatively-charged nucleophile or oxidant such as hydroxyl ions ($OH^-$) and peracetate ions ($RCOOO^-$), which are released from the sodium borate peracetate.

Figure 2:
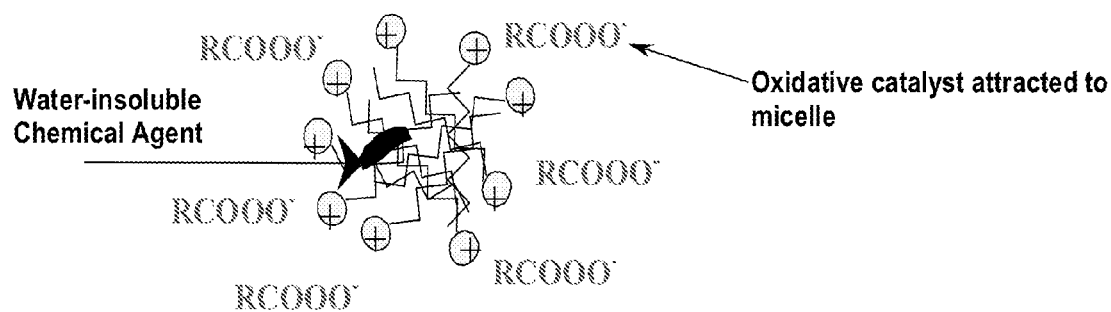
FIG. 2: Oxidative attack of a chemical agent with low water solubility within a cationic micelle in the decontamination formulation.

FIG. 2 shows an example of a cationic micelle that is formed from cationic surfactants. In the aqueous environment, the insoluble toxic chemical agent is dissolved within the micelle comprised of an aggregate of surfactant molecules with hydrophobic tails forming the interior core of the micelle, and hydrophilic heads concentrating at the surface of the micelle. These positively charged hydrophilic heads attract the negatively charged oxidant (in this case, the peracetate ion) greatly enhancing the reaction rates with the insoluble chemical agent within the micelle.

Figure 3:
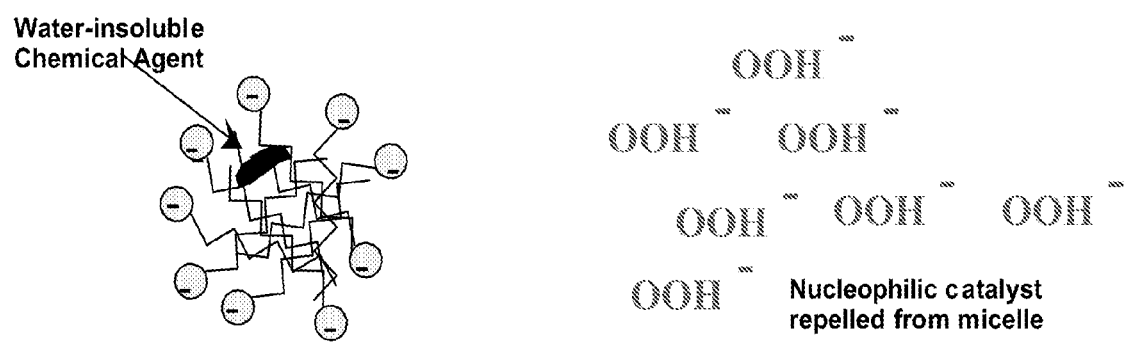
FIG. 3: Nucleophiles are repelled by anionic micelles and do not attack an insoluble toxic chemical agent.

This is contrasted with a formulation that is constructed with anionic surfactants such as those in a typical firefighting foam (FIG. 3). Here, the negatively charged micelles repel the nucleophiles and oxidants so that neutralization of the insoluble chemical agent, which is dissolved in the micelle, does not occur.

In the present invention, sodium borate peracetate is combined with a cationic surfactant. The use of cationic surfactants creates a reaction mixture that utilizes micellar catalysis to achieve rapid reaction rates against the agents. It also allows for the use of a relatively low percentage of ingredients in the formulation (i.e., a high percentage of water) as compared to other formulations that use a microemulsion (i.e., a high percentage of the formulation is ingredients other than water). In the present invention, the use of a high percentage of water allows the formulation to be concentrated in a dry form, and having a reduced weight.

Reduced Weight Decontamination Formulation Components

The reduced weight decontamination formulation consists of a mixture of the following components:
   Part A: Solid Sodium Borate Peracetate Material;
   Part B: Surfactant, Buffering, Foam Stabilizing, and Drying Ingredients; and
   Part C: Makeup Water—freshwater or saltwater supplied from a local source at the point of use A first example of a formulation for decontamination of chemical and biological warfare agents is shown below. An optimal pH of the formulation is 8.6. The formulation represents approximately an 80% weight savings over the pervious 'all-liquid' DF-200 formulation.

EXAMPLE #1

Part A (Sodium Borate Peracetate)
40 g Solid Sodium Borate Peracetate
Part B (Surfactant Buffering Foam Stabilizing and Drying Ingredients)
11 g Dodecyltrimethylammonium Chloride
4 g Tripropylene Glycol Methyl Ether
2 g 1-Dodecanol
10 g Potassium Bicarbonate
30 g Potassium Carbonate
20 g Sorbitol (Sorbigem™ Fines)
Part C (Makeup Water)
500 g Water (Freshwater or Saltwater).
Total=617 grams.
To prepare Part B, use the following method:
1. Add Tripropylene glycol methyl ether to an empty vessel.
2. Add dodecyltrimethylammonium chloride. Stir until dispersed throughout liquid and all lumps are dissolved.
3. Add 1-dodecanol. Stir (a paste will form).
4. Add sorbitol and stir.
5. Add potassium bicarbonate and potassium carbonate. A free flowing powder will result.
To prepare the formulation, use the following method.
1. Add Part C (makeup water) to an empty vessel.
2. Add Part A. Stir vigorously until dissolved.
3. Add Part B. Stir vigorously until dissolved.
4. The formulation is ready for use. The pH of the formulation should be approximately 8.6. Optimal deployment is through a compressed air foam generating system.

Example # 2 has the same ingredients as in Example #1, with the concentration shown in weight percentage (wt %) amounts:

EXAMPLE #2

Part A (Sodium Borate Peracetate)
6.5 wt % Solid Sodium Borate Peracetate
Part B (Surfactant, Buffering, Foam Stabilizing, and Drying Ingredients)
1.8 wt % Dodecyltrimethylammonium Chloride
0.6 wt % Tripropylene Glycol Methyl Ether
0.3 wt % 1-Dodecanol
1.6 wt % Potassium Bicarbonate
4.9 wt % Potassium Carbonate
3.3 wt % Sorbitol (Sorbigem™ Fines)
Part C (Makeup Water)
81.0 wt % Water (Freshwater or Saltwater)
Total=100%

Reduced weight DF-200 formulations can be packaged, stored, and transported to the point of use in the form of a two-part kit (i.e., Parts A and B, each packaged separately in individual containers). Then, at the point of use, the makeup water (Part C) is added.

Alternatively, the two pre-packaged dry parts (A and B) can be pre-mixed together to form a single dry mixture, however the storage stability may be reduced due to some interaction between the ingredients. This would not be a problem for some applications where a short shelf life would be acceptable.

The reduced weight formulation could also be used for other disinfection and neutralization applications where the toxic chemical or biological compounds are less resistant and/or less toxic than chemical warfare agents such as GD, VX, or HD or biological warfare agents such as anthrax spores. Examples of these applications include inactivation of viruses (e.g., avian influenza, smallpox, foot and mouth disease, etc.) or vegetative cells (e.g., $E.\ coli,\ salmonella$, etc.) or neutralization of toxic industrial chemicals (e.g., sodium cyanide). In this case, the concentrations of the ingredients of the formulation could be reduced in the ranges shown below:

EXAMPLE #3

Part A (Sodium Borate Peracetate)
5-40 g Solid Sodium Borate Peracetate
Part B (Surfactant, Buffering, Foam Stabilizing, and Drying Ingredients)
1-11 g Dodecyltrimethylammonium Chloride
0-4 g Tripropylene Glycol Methyl Ether
0-2 g 1-Dodecanol
5-40 g Potassium Bicarbonate
5-40 g Potassium Carbonate
0-20 g Sorbitol (Sorbigem™ Fines)
Part C (Makeup Water)
500 g Water (Freshwater or Saltwater)

Example # 4 has the same ingredients as in Example #3, with the concentration shown in weight percentage (wt %) amounts:

EXAMPLE #4

Part A (Sodium Borate Peracetate)
0.8-6.5 wt % Solid Sodium Borate Peracetate
Part B (Surfactant, Buffering, Foam Stabilizing, and Drying Ingredients)
0.1-1.8 wt % Dodecyltrimethylammonium Chloride
0-0.6 wt % Tripropylene Glycol Methyl Ether
0-0.3 wt % 1-Dodecanol
0.8-1.6 wt % Potassium Bicarbonate
0.8-4.9 wt % Potassium Carbonate
0-3.3 wt % Sorbitol (Sorbigem™ Fines)
Part C (Makeup Water)
81-97.5 wt % Water (Freshwater or Saltwater)
Total=100%

Substitutions for the various ingredients can be made. In Part B, the solvent (Tripropylene glycol methyl ether) can be replaced by other solvents, such as hexylene glycol, diethylene glycol methyl ether, or propylene glycol. In addition, the surfactant can be replaced by other cationic surfactants, such as other types of quaternary ammonium compounds (e.g., benzyl dodecyldimethyl ammonium chloride, didecyldimethylammonium chloride), amine alkoxylates (e.g., polyethylene glycol cocoamine), and amine oxides (e.g., lauric dimethylamine oxide). However, it was determined through a series of tests, that dodecyltrimethylammonium chloride provides superior efficacy as compared to other cationic surfactants so it is considered to be the surfactant for use in the preferred formulation. Potassium bicarbonate and potassium carbonate can be replaced by other buffering and pH adjustment ingredients including other bicarbonate and carbonate salts (e.g., sodium, ammonium, etc.), borate salts (e.g., sodium, potassium), phosphate salts (e.g., sodium and potassium), and acetate salts (e.g., sodium and potassium).

The sorbent additive, sorbitol, used as a drying ingredient, can also be replaced with another sorbent selected from the group consisting of zeolytes, precipitated silica, fumed silica, dendritic salt, sea salt, polyethylene glycol, urea, sodium gluconate, potassium gluconate, and polyols.

Examples of suitable polyols that may be used as the sorbent additive include

Sorbitol,
Mannitol,
Hydrogenated Starch Hydrolysates (HSH),
Maltitol,
Zylitol,
Lactitol Monohydrate,
Anhydrous Isomalt,
Erythritol, and
Polydextrose.

The polyols listed above are sugar-free sweeteners. They are carbohydrates, but they are not sugars. Chemically, polyols are considered polyhydric alcohols or "sugar alcohols" because part of the structure resembles sugar and part is similar to alcohols. However, these sugar-free sweeteners are neither sugars nor alcohols, as those words are commonly used. They are derived from carbohydrates whose carbonyl group (e.g., aldehyde or ketone, reducing sugar) has been reduced to a primary or secondary hydroxyl group.

The most widely used polyols in the food industry are sorbitol, mannitol, and malitol. Sorbitol is derived from glucose; mannitol from fructose; and malitol from high maltose corn syrup. Sorbogem™ and Mannigem™ are product names for sorbitol and mannitol sold by SPI Polyols, Inc., and are available in a wide range of particle size, down to fine sizes (i.e., Sorbogem Fines™).

Sorbitol is a hexahydric alcohol ($C_6H_{14}O_6$) corresponding to glucose, and has a molecular weight of 182.2. It occurs naturally, and is also produced by the hydrogenation of glucose syrup in the presence of Raney Nickel Catalyst. Some synonyms for sorbitol include: cholaxine, clucitol, diakarmon, gulitol, I-gulitol, karion, nivitin, sionit, sorbicolan, sorbite, d-sorbitol, sorbo, sorbol, sorbostyl, sorvilande. Sorbitol has a CAS No. 50-70-4 and an EC No. 200-061-5. The sorbent additive may be selected to be a "G.R.A.S." material, meaning that it is Generally Recognized As Safe to be used in this and other applications.

Efficacy Testing of the Reduced Weight Formulation

The performance of the preferred reduced weight decontamination formulation (Example #1) for neutralization of chemical agent simulants is shown in Table 1 with de-ionized water used as the make-up water (Part C). These tests were conducted in a solution of the formulation at a decon-to-simulant ratio of 200:1. The results are compared to the standard "all-liquid" version of DF-200.

TABLE 1

Concentration (wt %) of remaining simulant in solution tests of the reduced weight decontamination formulation Example #1.

| | VX Simulant | | | HD Simulant | | |
|---|---|---|---|---|---|---|
| Formulation | 1 Min. | 15 Min. | 60 Min. | 1 Min. | 15 Min. | 60 Min. |
| DF-200 (All-Liquid) | 81.6 | ND | >99.9 | 67.6 | 98.6 | ND |
| Reduced Weight Formulation Example #1 | 98.0 | 99.1 | >99.9 | 95.7 | 96.6 | ND |

Figure 4:
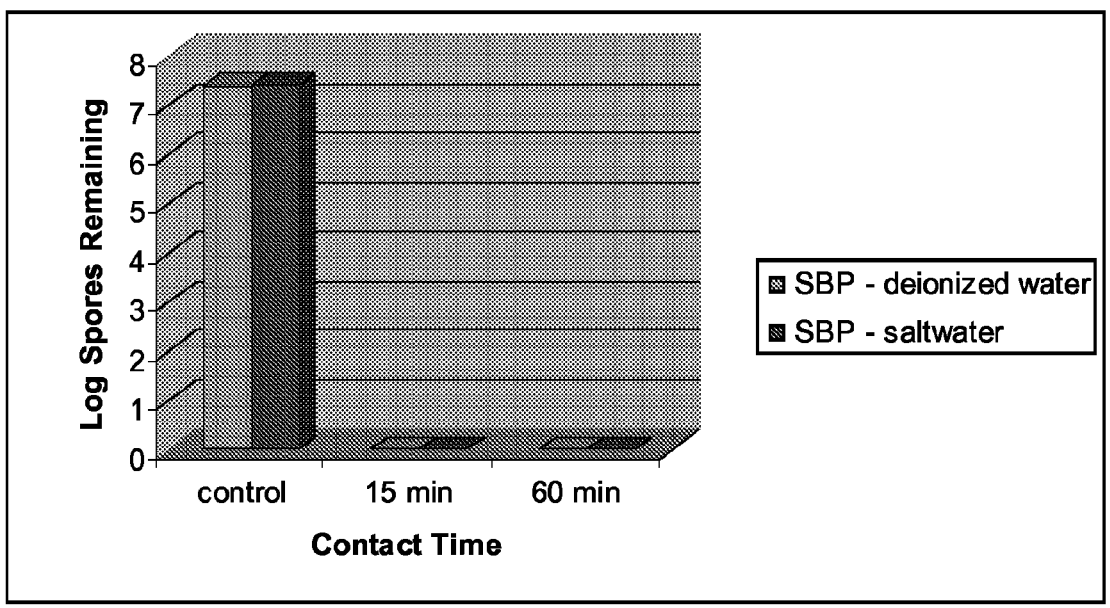
FIG. 4: Remaining spores following a 15 and 60 minute exposure to the reduced weight decontamination formulation with de-ionized water and saltwater as the make-up water.

Tests against the anthrax spore simulant (*Bacillus globigii* spores) demonstrated 99.9999% (7–log) kill after a 15 and 60 minute exposure to the preferred reduced weight decontamination formulation. The results are shown in FIG. 4.

In another example, the decontamination formulation can comprise:

by weight percentage:
0.8-6.5 wt % Solid Sodium Borate Peracetate;
0.1-1.8 wt % cationic surfactant;
0-0.6 wt % solvent;
0-0.3 wt % 1-Dodecanol;
0.8-6.5 wt % buffering agent;
0-3.3 wt % sorbent additive; and
water (remaining balance);
wherein the solvent is selected from the group consisting of Tripropylene glycol methyl ether, hexylene glycol, diethylene glycol methyl ether, and propylene glycol, and combinations thereof;
wherein the cationic surfactant is selected from the group consisting of dodecyltrimethylammonium chloride, benzyl dodecyldimethylammonium chloride, didecyldimethylammonium chloride, amine alkoxylates, polyethylene glycol cocoamine, amine oxides, and lauric dimethylamine oxide, and combinations thereof;
wherein the buffering agent is selected from the group consisting of sodium bicarbonate and carbonate salts, ammonium bicarbonate and carbonate salts, sodium or potassium borate salts, sodium or potassium borate phosphate salts, and sodium or potassium acetate salts, and combinations thereof; and
wherein the sorbent additive is selected from the group consisting of selected from the group consisting of zeolytes, precipitated silica, fumed silica, dendritic salt, sea salt, polyethylene glycol, urea, sodium gluconate, potassium gluconate, and polyols, and combinations thereof.

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A dry decontamination pre-packaged two-part kit comprising,

Part A (dry) comprises:
Solid Sodium Borate Peracetate ingredient; and

Part B (dry) comprises:
cationic surfactant dodecyltrimethylammonium chloride, benzyl dodecyldimethylammonium chloride, didecyldimethylammonium chloride, and combinations thereof;
solvent selected from the group consisting of tripropylene glycol methyl ether, hexylene glycol, diethylene glycol methyl ether, and propylene glycol, and combinations thereof;
1-Dodecanol;
buffering agent selected from the group consisting of sodium bicarbonate and carbonate salts, ammonium bicarbonate and carbonate salts, sodium or potassium borate salts, sodium or potassium borate phosphate salts, and sodium or potassium acetate salts, and combinations thereof; and
sorbent additive selected from the group consisting of selected from the group consisting of zeolites, precipitated silica, fumed silica, dendritic salt, sea salt, polyethylene glycol, urea, sodium gluconate, potassium gluconate, and polyols, and combinations thereof;

wherein when said Part A and Part B are mixed with 500 g water as Part C to form a solution, said solution would result in concentrations of the aqueous solution:
- 0.8-6.5 wt % Solid Sodium Borate Peracetate;
- 0.1-1.8 wt % cationic surfactant;
- 0-0.6 wt % solvent;
- 0-0.3 wt % 1-Dodecanol;
- 0.8-6.5 wt % buffering agent; and
- 0-3.3 wt % sorbent additive.

2. The dry two-part decontamination kit of claim 1, wherein the sorbent additive is a polyol selected from the group consisting of sorbitol, mannitol, hydrogenated starch hydrolysates (HSH), maltitol, zylitol, lactitol monohydrate, anhydrous isomalt, erythritol, and polydextrose, and combinations thereof.

3. The dry two-part decontamination kit of claim 1, wherein when said Part A and Part B are mixed with 500 g water as Part C to form a solution, said solution would result in an aqueous solution having a pH of about 8.6.

4. A dry decontamination two-part pre-packaged kit, comprising all-dry Parts A and B, to be mixed with Part C (water) in the field at the point of use, wherein:
Part A (dry) comprises:
- 5-40 g Solid Sodium Borate Peracetate ingredient; and Part B (dry) comprises:
- 1-11 g Dodecyltrimethylammonium Chloride,
- 0-4 g Tripropylene Glycol Methyl Ether;
- 0-2 g 1-Dodecanol;
- 5-40 g Potassium Bicarbonate;
- 5-40 g Potassium Carbonate, and
- 0-20 g Sorbitol ingredients.

5. The dry two-part decontamination kit of claim 4, wherein when said Part A and Part B are mixed with 500 g water as Part C to form a solution, said solution would result in concentrations of the aqueous solution:
- 0.8 wt % Solid Sodium Borate Peracetate;
- 0.1 wt % Dodecyltrimethylammonium Chloride;
- 0.8 wt % Potassium Bicarbonate; and
- 0.8 wt % Potassium Carbonate.

6. The dry two-part decontamination kit of claim 4, wherein when said Part A and Part B are mixed with 500 g water as Part C to form a solution, said solution would result in concentrations of the aqueous solution:
- 6.5 wt % Solid Sodium Borate Peracetate;
- 1.8 wt % Dodecyltdmethylammonium Chloride;
- 0.6 wt % Tripropylene Glycol Methyl Ether;
- 0.3 wt % 1-Dodecanol;
- 1.6 wt % Potassium Bicarbonate;
- 4.9 wt %, Potassium Carbonate; and
- 3.3 wt % Sorbitol.

7. The dry two-part decontamination kit of claim 6, wherein when said Part A and Part B are mixed with 500 g water as Part C to form a solution, said solution would result in an aqueous solution having a pH of about 8.6.

8. The dry two-part decontamination kit of claim 4, wherein when said Part A and Part B are mixed with 500 g water as Part C to form a solution, said solution would result in an aqueous solution having a pH of about 8.6.

9. The dry two-part decontamination kit of claim 4, wherein the dry Part B component is prepared according to the following steps, performed in the order listed:
a) add the Tripropylene glycol methyl ether to an empty vessel;
b) add the dodecyltrimethylammonium chloride and stir until dispersed throughout liquid and all lumps are dissolved;
c) add the 1-dodeeanol and stir until a paste forms;
d) add the sorbitol and stir;
e) add the potassium bicarbonate and potassium carbonate ingredients, resulting in free flowing powder.

10. The dry, pre-packaged decontamination formulation according to claim 4, comprising, all-dry Parts A and B having concentrations of the dry components,
wherein when said Part A and Part B are mixed with 500 g water as Part C to form a solution, said solution would result in concentrations of the aqueous solution:
- 0.8-6.5 wt % Solid Sodium Borate Peracetate;
- 0.1-1.8 wt % Dodecyllrimethylammonium Chloride;
- 0-0.6 wt % Tripropylene Glycol Methyl Ether;
- 0-0.3 wt % 1-Dodecanol;
- 0.8-1.6 wt % Potassium Bicarbonate;
- 0.8-4.9 wt % Potassium Carbonate; and
- 0-3.3 wt % Sorbitol.

* * * * *